US012808826B2

(12) United States Patent
Nakao

(10) Patent No.: US 12,808,826 B2
(45) Date of Patent: Nov. 24, 2026

(54) SENSITIVE MEMBRANE AND GAS SENSOR

(71) Applicant: Panasonic Intellectual Property Management Co., Ltd., Osaka (JP)

(72) Inventor: Atsuo Nakao, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 354 days.

(21) Appl. No.: 18/550,078

(22) PCT Filed: Mar. 16, 2022

(86) PCT No.: PCT/JP2022/012098
§ 371 (c)(1),
(2) Date: Sep. 11, 2023

(87) PCT Pub. No.: WO2022/196744
PCT Pub. Date: Sep. 22, 2022

(65) Prior Publication Data
US 2024/0183813 A1 Jun. 6, 2024

(30) Foreign Application Priority Data
Mar. 19, 2021 (JP) ................................ 2021-046555

(51) Int. Cl.
*G01N 27/12* (2006.01)
*G01N 33/00* (2006.01)

(52) U.S. Cl.
CPC ....... *G01N 27/125* (2013.01); *G01N 33/0027* (2013.01)

(58) Field of Classification Search
CPC ......................... G01N 27/125; G01N 33/0027
See application file for complete search history.

(56) References Cited

U.S. PATENT DOCUMENTS

| | | | | |
|---|---|---|---|---|
| 3,983,527 | A | 9/1976 | Ohsato et al. | |
| 4,631,952 | A | 12/1986 | Donaghey | |
| 4,942,364 | A | 7/1990 | Nishijima et al. | |
| 5,256,574 | A | 10/1993 | Neuburger et al. | |
| 5,456,750 | A | 10/1995 | Mackay et al. | |
| 5,474,743 | A * | 12/1995 | Trend | C07D 498/18 422/82.07 |
| 6,471,763 | B1 | 10/2002 | Karl | |
| 2003/0219373 | A1 | 11/2003 | Foster | |

(Continued)

FOREIGN PATENT DOCUMENTS

| | | |
|---|---|---|
| CN | 112300578 A | 2/2021 |
| JP | S50-038236 A | 4/1975 |

(Continued)

OTHER PUBLICATIONS

English translation of WO-2018221632, accessed from iq.ip.com (Year: 2018).*

(Continued)

*Primary Examiner* — David Z Huang
*Assistant Examiner* — Jean F Morello
(74) *Attorney, Agent, or Firm* — Rimon P.C.

(57) ABSTRACT

A sensitive membrane includes: a membrane body containing a sensitive material; and a carbon black contained in the membrane body. The carbon black has a volatile content equal to or greater than 2.5 wt %. This sensitive membrane may detect even a very small amount of odor molecules.

10 Claims, 7 Drawing Sheets

(56) References Cited

U.S. PATENT DOCUMENTS

| | | | |
|---|---|---|---|
| 2004/0202856 | A1 | 10/2004 | Blok |
| 2008/0125335 | A1 | 5/2008 | Bhavsar |
| 2009/0155157 | A1 | 6/2009 | Stenger et al. |
| 2009/0236566 | A1 | 9/2009 | Nishiura et al. |
| 2010/0219849 | A1 | 9/2010 | McCoy et al. |
| 2021/0063337 | A1 | 3/2021 | Dong et al. |

FOREIGN PATENT DOCUMENTS

| | | | | |
|---|---|---|---|---|
| JP | H02-049149 | A | 2/1990 | |
| JP | H05-036357 | U | 5/1993 | |
| JP | H11-094784 | A | 4/1999 | |
| JP | H11-349849 | A | 12/1999 | |
| JP | 2002-509609 | A | 3/2002 | |
| JP | 2004-510953 | A | 4/2004 | |
| JP | 2004-193256 | A | 7/2004 | |
| JP | 2004-211012 | A | 7/2004 | |
| JP | 2004-340945 | A | 12/2004 | |
| JP | 2006-058766 | A | 3/2006 | |
| JP | 2006-182818 | A | 7/2006 | |
| JP | 2009-138103 | A | 6/2009 | |
| JP | 2010-038692 | A | 2/2010 | |
| JP | 2011-506656 | A | 3/2011 | |
| JP | 2014-241279 | A | 12/2014 | |
| JP | 2016-167442 | A | 9/2016 | |
| JP | 2019-036378 | A | 3/2019 | |
| WO | 99/01733 | A1 | 1/1999 | |
| WO | 01/50117 | A1 | 7/2001 | |
| WO | 2014/185452 | A1 | 11/2014 | |
| WO | 2017/119428 | A1 | 7/2017 | |
| WO | WO-2018221632 | A1 * | 12/2018 | ............. H01G 11/24 |
| WO | 2019/189245 | A1 | 10/2019 | |

OTHER PUBLICATIONS

English translation of JP2004211012, accessed from iq.ip.com (Year: 2004).*

Mark C. Lonergan et al., “Array-based vapor sensing using chemically sensitive, carbon black-polymer resistors”, Chem. Mater, 1996, 8, pp. 2298-2312 (Year: 1996).

Non-Final Office Action dated Jun. 4, 2025 issued in related U.S. Appl. No. 18/252,451.

Non-Final Office Action dated Jun. 4, 2025 issued in related U.S. Appl. No. 18/550,085.

International Search Report dated Jun. 7, 2022 issued in International Patent Application No. PCT/JP2022/012098, with English translation.

International Search Report dated Jun. 7, 2022 issued in International Patent Application No. PCT/JP2022/012099, with English translation.

International Search Report dated Jun. 7, 2022 issued in International Patent Application No. PCT/JP2022/011854, with English translation.

Nagashima, Kazuki et al. Innovative Molecular Recognition Sensing by Nanowires with Robust Molecular Fingerprint. Proceedings of the 100th CSJ Annual Spring Meeting, Mar. 5, 2020, vol. 100, 1PC-085.

Wyszynski et al., “Array of Chemosensitive Resistors with Composites of Gas Chromatography (GC) Materials and Carbon Black for Detection and Recognition of VOCs: An Optimization Study”, All Sensors 2018, The Third International Conference on Advances in Sensors, Actuators, Metering and Sensing, pp. 28-32 (Year: 2018).

Jan-Chan Huang, “Carbon Black Filled Conducting Polymers and Polymer Blends”, Advances in Polymer Technology, 2002, vol. 21, No. 4., pp. 299-313 (Year: 2002).

Final Office Action dated Nov. 20, 2025 issued in U.S. Appl. No. 18/282,451.

Final Office Action dated Nov. 20, 2025 issued in U.S. Appl. No. 18/550,085.

Office Action received in U.S. Appl. No. 18/550,085, dated Apr. 8, 2026.

Notice of Reasons for Refusal received in corresponding Japanese Patent Application No. 2023-507168, dated Apr. 21, 2026.

Notice of Allowance received in U.S. Appl. No. 18/282,451, dated Jul. 24, 2026.

* cited by examiner

SENSITIVE MEMBRANE AND GAS SENSOR

CROSS-REFERENCE OF RELATED APPLICATIONS

This application is the U.S. National Phase under 35 U.S.C. § 371 of International Patent Application No. PCT/JP2022/012098, filed on Mar. 16, 2022, which in turn claims the benefit of Japanese Patent Application No. 2021-046555, filed on Mar. 19, 2021, the entire disclosures of which Applications are incorporated by reference herein.

TECHNICAL FIELD

The present disclosure generally relates to a sensitive membrane and a gas sensor. More particularly, the present disclosure relates to a sensitive membrane including a membrane body containing a sensitive material and a carbon black contained in the membrane body and a gas sensor.

BACKGROUND ART

Patent Literature 1 discloses a sensor for use in an artificial olfactory system. This sensor detects an analyte in a fluid, includes a layer containing conductive modification particles, and is electrically connected to an electrical measuring device. The conductive modification particles include a carbon black having at least one organic group.

As for a sensor of this type, there has been an increasing demand for increasing its sensitivity to allow the sensor to detect even a very small amount of odor molecules.

CITATION LIST

Patent Literature

Patent Literature 1: JP 2004-510953 A

SUMMARY OF INVENTION

An object of the present disclosure is to provide a sensitive membrane usable as a material for a high-sensitivity gas sensor and also provide a gas sensor including such a sensitive membrane.

A sensitive membrane according to an aspect of the present disclosure includes: a membrane body containing a sensitive material; and a carbon black contained in the membrane body. The carbon black has a volatile content equal to or greater than 2.5 wt %.

A gas sensor according to another aspect of the present disclosure includes: the sensitive membrane described above; and an electrode electrically connected to the sensitive membrane.

DESCRIPTION OF EMBODIMENTS

Embodiment (1) Overview

Figure 1A:
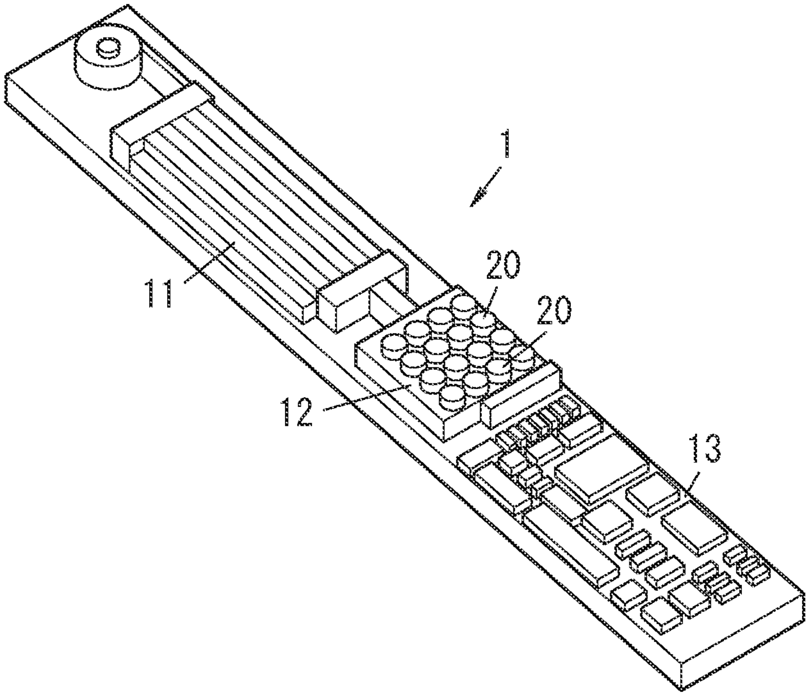
FIG. 1A is a perspective view illustrating a gas sensor according to an exemplary embodiment of the present disclosure.

FIG. 1A illustrates a schematic configuration for a gas sensor 1 according to an exemplary embodiment of the present disclosure. The gas sensor 1 may be used to, for example, detect odor molecules as detection target molecules. Examples of the odor molecules include volatile organic compounds (VOCs) and ammonia. The gas sensor 1 is used to detect VOCs as detection target molecules. The gas sensor 1 detects VOCs as odor molecules included in a sample gas such as a gas taken from a food, a breath taken from a human body, or the air taken from a building room. Note that the detection target molecules to be detected by the gas sensor 1 do not have to be VOCs but may also be multiple types of odor molecules including VOCs or non-odor molecules such as molecules of a flammable gas or a poisonous gas like carbon monoxide.

As shown in FIG. 1A, the gas sensor 1 includes a supply unit 11, a sensor unit 12, and a processing unit 13. The supply unit 11 supplies a sample gas including odor molecules and a reference gas to the sensor unit 12. The sensor unit 12 includes a plurality of sensitive membranes 20 and a plurality of electrodes 21. The processing unit 13 includes a detection unit for detecting a variation in the resistance value measured by the sensor unit 12 and a control unit for controlling the operation of the gas sensor 1. The supply unit 11 includes piping through which the sample gas and the reference gas circulate. The processing unit 13 includes electric circuits serving as the detection unit and the control unit.

Figure 1B:
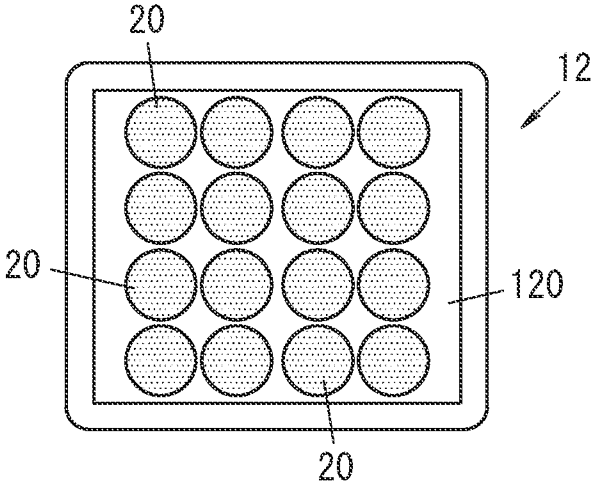
FIG. 1B is a plan view illustrating a sensor unit of the gas sensor.

As shown in FIG. 1B, the sensor unit 12 is formed by providing a plurality of sensitive membranes 20 on a substrate 120. A number of sensitive membranes 20 are arranged vertically and horizontally to form an array (e.g., a 4×4 array in this embodiment) of sensitive membranes 20. Each of these sensitive membranes 20 is formed in a circular pattern in plan view. Note that the number, arrangement, and shape of the sensitive membranes 20 in the sensor unit 12 do not have to be the ones shown in FIG. 1B but may also be changed as appropriate according to the type of the gas sensor 1, for example.

Figure 1C:
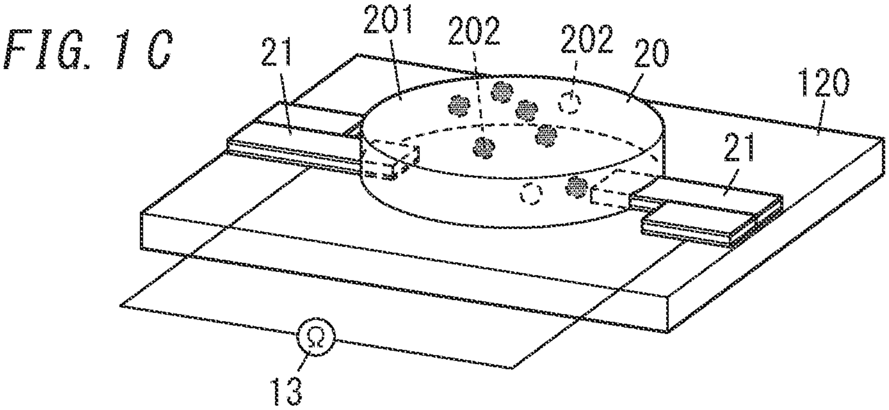
FIG. 1C is a perspective view illustrating a sensitive membrane of the gas sensor.

As shown in FIG. 1C, each sensitive membrane 20 includes a membrane body 201 and conductive particles 202. The conductive particles 202 are dispersed in the matrix of the membrane body 201.

The membrane body 201 contains a sensitive material. An appropriate sensitive material is selected according to, for example, the type of the chemical substance to be adsorbed by the membrane body 201 and/or the type of the conductive particles 202. The sensitive material may be an organic material having electrical insulation properties and includes, for example, at least one material selected from the group consisting of high molecular (macromolecular) materials and low molecular materials. The sensitive material preferably includes a high molecular material, in particular. Note that if the sensitive material includes a high molecular material, the membrane body 201 may have heat resistance.

Examples of preferred sensitive materials include materials commercially available as stationary phases for columns in gas chromatographs. More specifically, the sensitive material may include, for example, at least one material selected from the group consisting of polyalkylene glycols, polyesters, silicones, glycerols, nitriles, dicarboxylic acid monoesters, and aliphatic amines. This allows the membrane body 201 to easily adsorb chemical substances (volatile organic compounds, in particular) in the gas.

The polyalkylene glycols include, for example, polyethylene glycol (with a heat resistant temperature of 170° C.). The polyesters include, for example, at least one material selected from the group consisting of poly(diethylene glycol adipate) and poly(ethylene succinate). The silicones include, for example, at least one material selected from the group consisting of dimethyl silicone, phenylmethyl silicone, trifluoropropyl methyl silicone, and cyanosilicone (with a heat resistant temperature of 275° C.). The glycerols include, for example, diglycerol (with a heat resistant temperature of 150° C.). The nitriles include at least one material selected from the group consisting of, for example, N,N-bis (2-cyanoethyl) formamide (with a heat resistant temperature of 125° C.) and 1,2,3-tris (2-cyanoethoxy) propane (with a heat resistant temperature of 150° C.). The dicarboxylic acid monoesters include at least one material selected from the group consisting of, for example, nitro terephthalic acid-modified polyethylene glycol (with a heat resistant temperature of 275° C.) and diethylene glycol succinate (with a heat resistant temperature of 225° C.). The aliphatic amines include, for example, tetra hydroxyethyl ethylenediamine (with a heat resistant temperature of 125° C.).

The conductive particles 202 are particles that form a carbon black. The carbon black is an aggregate of ultrafine spherical particles formed through incomplete combustion of a compound including either hydrocarbon or carbon. Optionally, the membrane body 201 may include, as particles with electrical conductivity, not only the carbon black but also at least one material selected from the group consisting of conductive polymers, metals, metal oxides, semiconductors, superconductors, and complex compounds.

A pair of electrodes 21 are connected to the sensitive membrane 20. Each of these electrodes 21 is electrically connected to the conductive particles 202 in the sensitive membrane 20. The pair of electrodes 21 are also electrically connected to the detection unit of the processing unit 13.

Figure 2A:
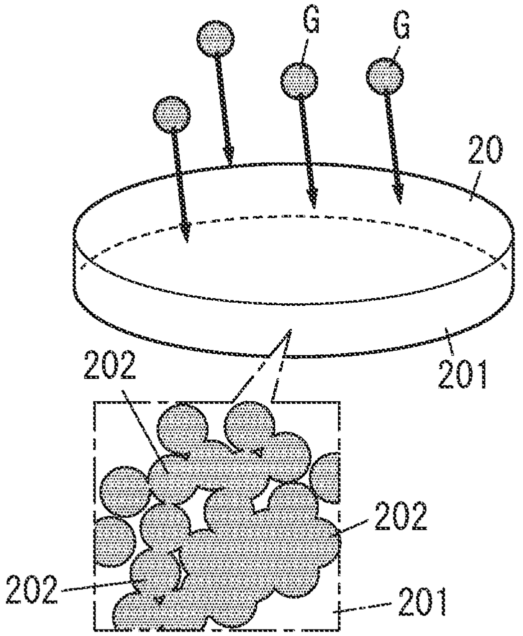
FIGS. 2A and 2B illustrate how the sensitive membrane of the gas sensor operates.
Figure 2B:
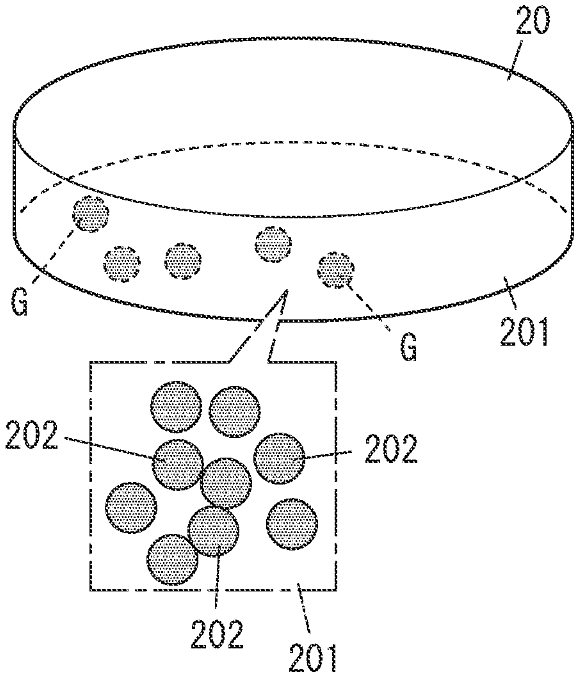
Figure 2C:
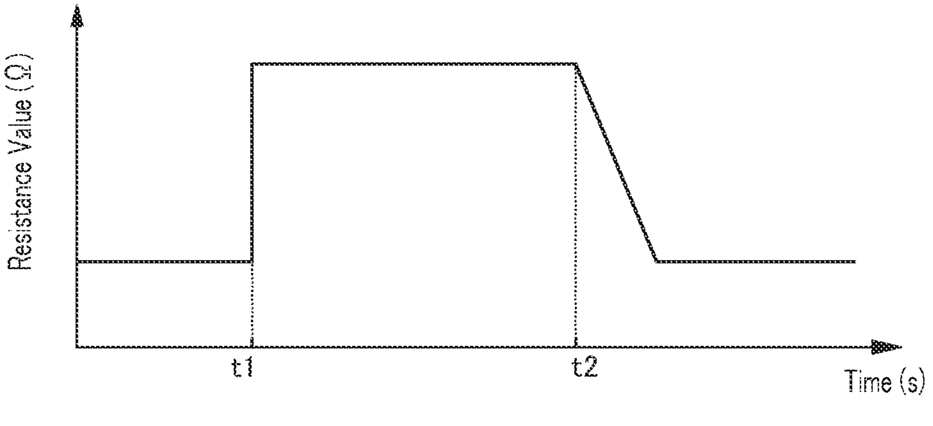
FIG. 2C is a graph showing how the resistance value may change with time through the operation of the sensitive membrane of the gas sensor.

In such a sensitive membrane 20, the membrane body 201 is less thick before adsorbing the odor molecules G as shown in FIG. 2A. That is to say, the plurality of conductive particles 202 are dispersed more densely in the membrane body 201. Once the sensitive membrane 20 has adsorbed the odor molecules G, the membrane body 201 expands to have an increased thickness. That is to say, the plurality of conductive particles 202 are dispersed more sparsely in the membrane body 201 (refer to FIG. 2B). As a result, the sensitive membrane 20 comes to have an increased resistance value when adsorbing the odor molecules G at a time t1 as shown in FIG. 2C. Meanwhile, as the odor molecules G desorb from the sensitive membrane 20, the membrane body 201 of the sensitive membrane 20 shrinks to have a decreased thickness. As a result, the resistance value of the sensitive membrane 20 gradually decreases since a time t2 when the odor molecules G start to desorb. The gas sensor 1 may determine, by making the detection unit of the processing unit 13, which is electrically connected to the electrodes 21, detect this change in the resistance value, whether there are any odor molecules G in the sample gas supplied from the supply unit 11 to the sensor unit 12.

(2) Details

In general, there are two types of carbon blacks, namely, a "conductive carbon black" and a "coloring carbon black." The conductive carbon black is mainly used as a conductive material in various fields for films, IC trays, sheet heating elements, magnetic tapes, and conductive rubber. The coloring carbon black is mainly used as a black pigment in various fields for newspaper inks, printing inks, resin coloring, paints, and toners. The conductive carbon black and the coloring carbon black may be distinguished by the degree of development of a network structure (i.e., so-called "structure") formed by carbon black particles (conductive particles 202). The conductive carbon black has a well-developed structure, while the coloring carbon black has a structure which is developed less fully than the conductive carbon black. That is to say, the structure is formed by bonding carbon black particles together both chemically and physically. The carbon black with the well-developed structure has many carbon black particles that are chemically and physically bonded together. On the other hand, the carbon black with an undeveloped structure has a smaller number of carbon black particles that are bonded together chemically and physically.

In this embodiment, a carbon black with an undeveloped structure is preferably used as the carbon black. Specifically, in this embodiment, a carbon black having a dibutyl phthalate absorption number (hereinafter referred to as a "DBP absorption number") less than 100 $cm^3$/100 g is preferably used as the carbon black. Meanwhile, a carbon black having a DBP absorption number equal to or greater than 100 $cm^3$/100 g has a well-developed structure, and therefore, is preferably not used in this embodiment. Note that the DBP absorption number herein refers to the number of DBP (dibutyl phthalate) particles absorbed into 100 g of carbon black and is measured in accordance with the JIS K 6221 standard.

According to another method for evaluating the degree of development of the structure, a Stokes mode diameter (Dst) of an aggregate as measured by centrifugal sedimentation analysis may also be used. Specifically, a value calculated by the following method may be used as Dst.

Specifically, a sample solution with a carbon black concentration of 0.01 wt % is prepared by adding a precisely weighed carbon black to a 20% ethanol aqueous solution containing a surfactant. The carbon black is sufficiently dispersed in the sample solution with ultrasonic waves and a solution thus prepared is used as a measurement sample. On the other hand, 10 ml of spin liquid (pure water) is injected into a particle size distribution analyzer that uses centrifugal sedimentation, 1 ml of buffer solution (20 vol % ethanol aqueous solution) is further injected thereto, and then 1 ml of the measurement sample prepared as described above is injected thereto. The Stokes equivalent diameter is measured by centrifugal sedimentation at a number of revolutions of 6000 rpm. Thereafter, a histogram representing a relative frequency of occurrence is plotted with respect to the Stokes equivalent diameters thus measured. In the histogram thus plotted, a Stokes equivalent diameter at the maximum frequency is regarded as Dst.

Meanwhile, the mean primary particle size (D0) of the carbon black may be calculated by observing the carbon black particles (conductive particles 202) in the sensitive membrane 20 through an electron microscope.

There is correlation between the DBP absorption number and the Dst/D0 ratio. A Dst/D0 ratio less than 4 corresponds to a DBP absorption number less than 100 $cm^3$/100 g.

As for the mechanism that causes a carbon black to have electrical conduction in a polymer matrix (such as the membrane body 201), there are two competitive theories, namely, a so-called "conductive passage theory," according to which x electrons move through the structure, and a so-called "tunneling effect theory," according to which electrical conduction is produced by causing x electrons to jump through the gap between the particles. The carbon black having a DBP absorption number equal to or greater than 100 $cm^3$/100 g has such a developed structure that the electrical conduction through the conductive passage would be prevailing. On the other hand, the carbon black having a DBP absorption number less than 100 $cm^3$/100 g has such an undeveloped structure that the electrical conduction due to the tunneling effect would be prevailing.

Figure 3:
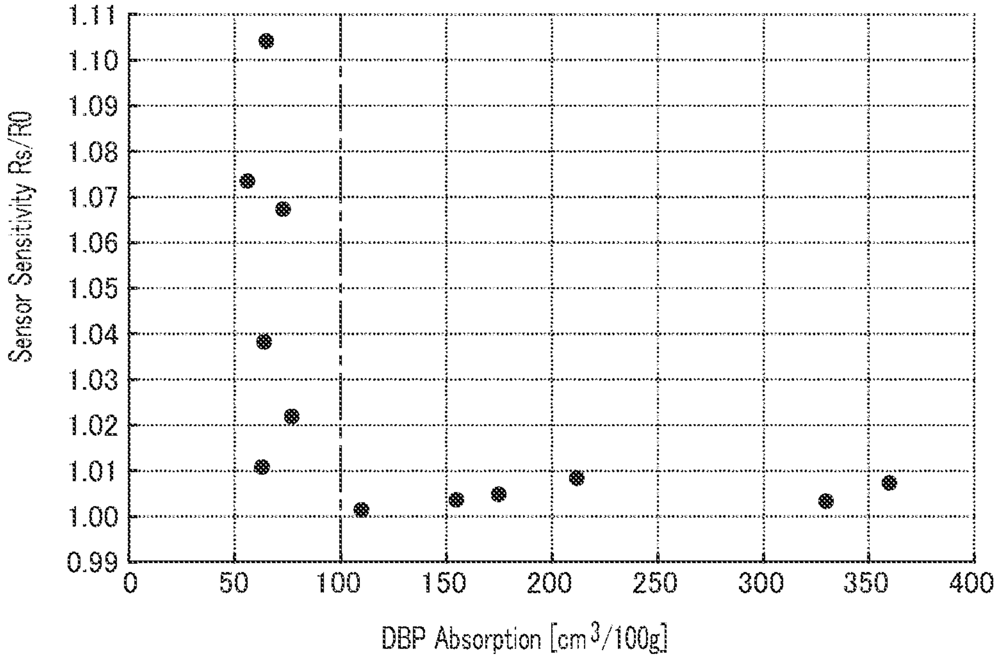
FIG. 3 is a graph showing how the sensor sensitivity changes with a DBP absorption number of the gas sensor.

In the sensitive membrane 20 according to this embodiment, the electrical conduction would be produced by the tunneling effect of the carbon black, thus causing the resistance value to change more significantly due to adsorption of the odor molecules G and thereby allowing the gas sensor 1 to have higher sensitivity. FIG. 3 shows how the sensor sensitivity changes with the DBP absorption number of a carbon black as a material. The sensor sensitivity is given by Rs/R0, where Rs is the resistance value measured on the sensitive membrane 20 when an evaluation gas is introduced into the gas sensor 1 and R0 is the resistance value measured on the sensitive membrane 20 when an odorless gas is introduced into the gas sensor 1. As the sensitive material for the membrane body 201, bis cyanopropyl-cyanopropylphenyl polysiloxane (product name SP-2330 manufactured by Sigma-Aldrich) is used. As the evaluation gas, benzaldehyde is used. The content of the carbon black in the sensitive membrane 20 is constant.

As is clear from FIG. 3, when a carbon black having a DBP absorption number less than 100 $cm^3$/100 g is used, the sensor sensitivity Rs/R0 increases. On the other hand, when a carbon black having a DBP absorption number equal to or greater than 100 $cm^3$/100 g is used, the sensor sensitivity Rs/R0 does not exceed around 1.01. Thus, according to this embodiment, a carbon black having a DBP absorption number less than 100 $cm^3$/100 g and an undeveloped structure is preferably used. A lower limit of the DBP absorption number of the carbon black is not set at any particular value but is preferably equal to or greater than 50 $cm^3$/100 g. In that case, Dst/D0 will be equal to or greater than 2.

Figure 4:
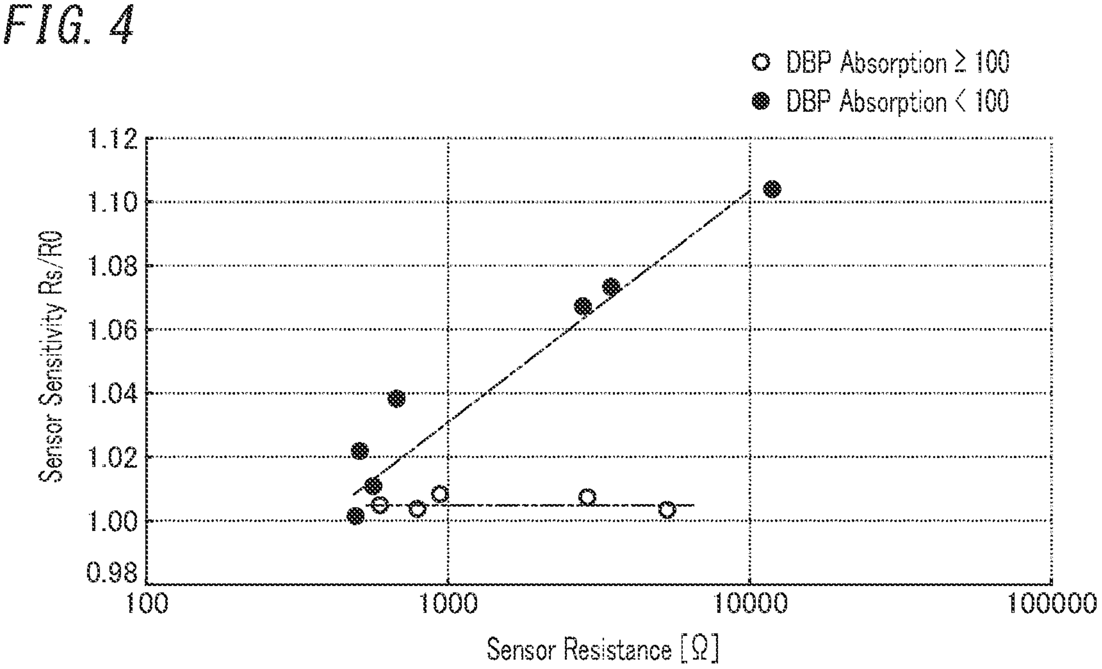
FIG. 4 is a graph showing how the sensor sensitivity changes with the sensor resistance of the gas sensor.

Also, when a carbon black having a DBP absorption number less than 100 $cm^3$/100 g is used, as the sensor resistance increases, the sensor sensitivity Rs/R0 rises as shown in FIG. 4. On the other hand, when a carbon black having a DBP absorption number equal to or greater than 100 $cm^3$/100 g is used, the sensor sensitivity Rs/R0 does not increase from around 1.01, even if the sensor resistance increases. That is why in this embodiment, a carbon black having a DBP absorption number less than 100 $cm^3$/100 g and an undeveloped structure is preferably used.

Figure 5A:
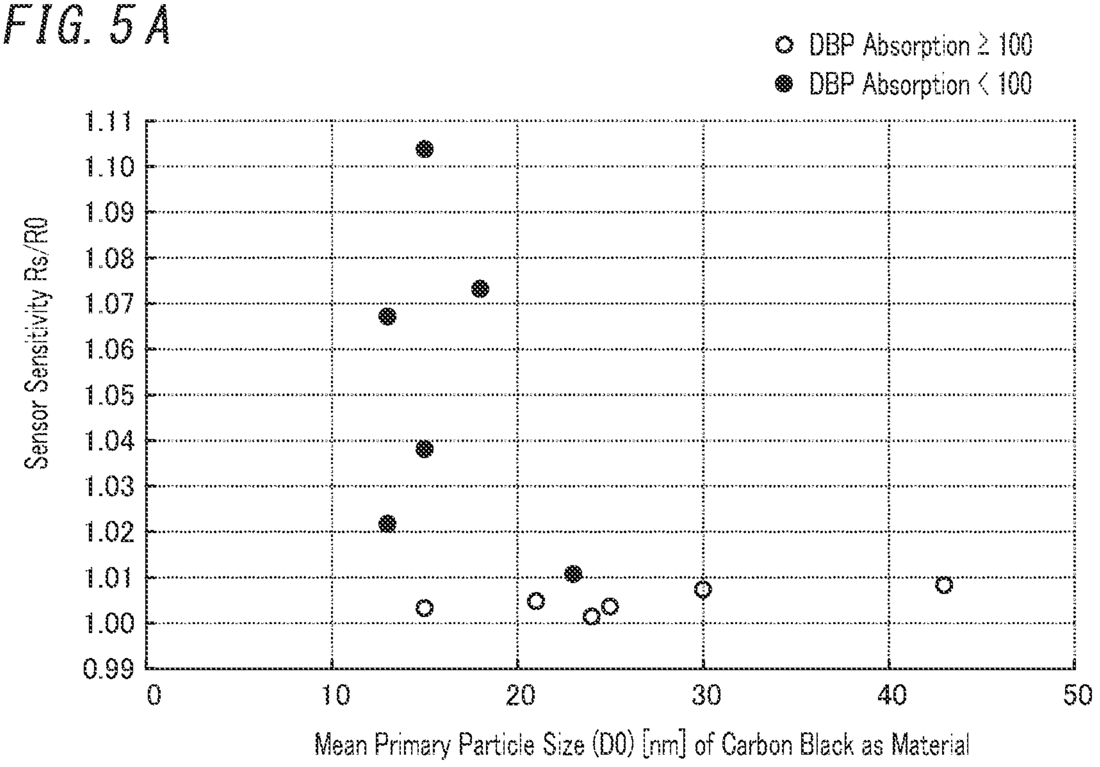
FIG. 5A is a graph showing how the sensor sensitivity changes with the mean primary particle size (D0) of a carbon black as a material for the gas sensor.

FIG. 5A shows how the sensor sensitivity Rs/R0 changes with the mean primary particle size (D0) of the carbon black as a material. The sensor sensitivity Rs/R0 would not be so closely correlated with the mean primary particle size (D0) of the carbon black. That is to say, the sensor sensitivity Rs/R0 would be affected more significantly by the DBP absorption number rather than the mean primary particle size (D0) of the carbon black. Nevertheless, the sensor sensitivity Rs/R0 would improve if the mean primary particle size (D0) of the carbon black is equal to or greater than 10 nm and equal to or less than 20 nm. Note that the mean primary particle size (D0) of the carbon black as a material is an arithmetic mean particle size calculated by observing the carbon black particles (conductive particles 202) through an electron microscope.

Figure 5B:
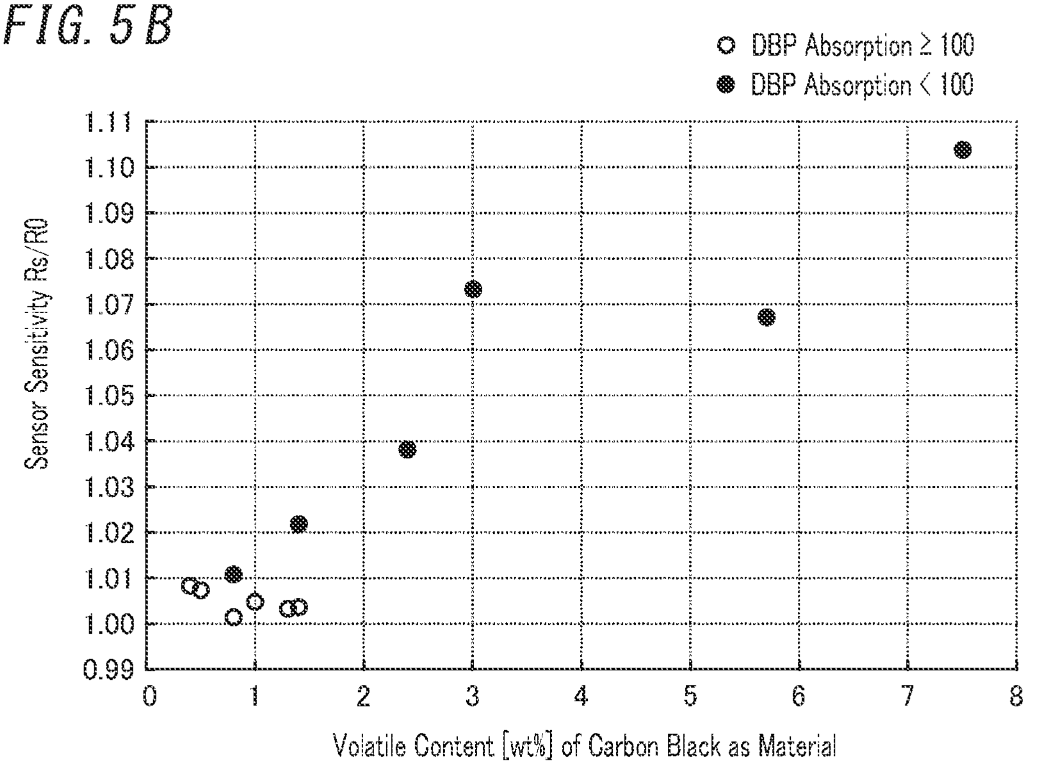
FIG. 5B is a graph showing how the sensor sensitivity changes with the volatile content of the carbon black as the material for the gas sensor.
Figure 6A:
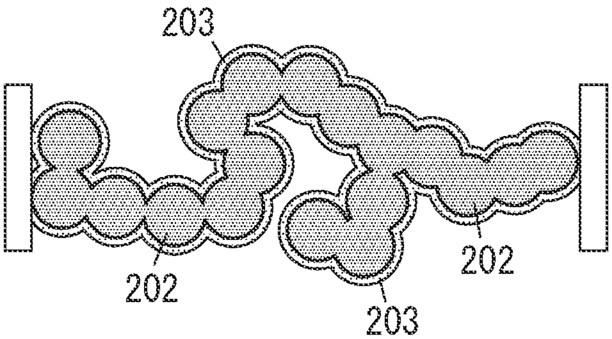
FIGS. 6A and 6B illustrate structures of the carbon black as the material for the gas sensor.
Figure 6B:
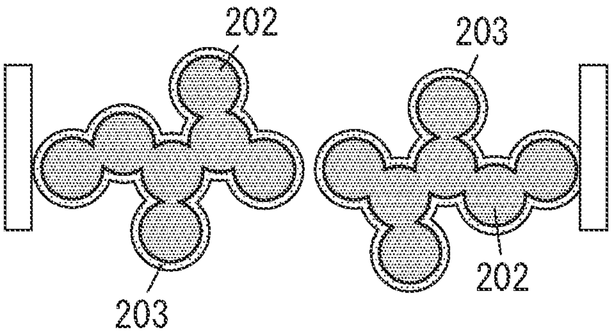
Figure 6C:
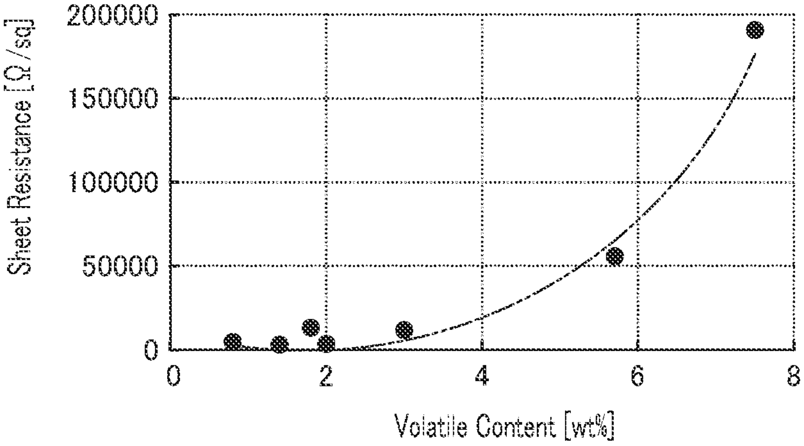
FIG. 6C is a graph showing how the sheet resistance changes with the volatile content of the carbon black as the material for the gas sensor.

FIG. 5B shows how the sensor sensitivity Rs/R0 changes with the volatile content of the carbon black as a material. There are surface functional groups on the surface of the carbon black particles (conductive particles 202). Examples of the surface functional groups include a carboxyl group, a hydroxyl group, and a quinone group. FIG. 6A schematically illustrates a carbon black with a developed structure. FIG. 6B schematically illustrates a carbon black with an undeveloped structure. The reference sign 203 denotes the surface functional groups of the carbon black particles (conductive particles 202). FIG. 6C shows how the sheet resistance changes with the volatile content of the carbon black. The results shown in FIG. 6C indicate that as the volatile content of the carbon black increases, the sheet resistance of a thin film or film containing the carbon black rises. In general, the larger the number of the surface functional groups of the carbon black is, the higher its volatile content is. That is to say, as the volatile content of the carbon black increases, the number of the surface functional groups increases as well, thus causing the number of surface functional groups to have a significant effect on the sheet resistance.

FIG. 5B shows the effect of the sensor sensitivity Rs/R0 on the number of the surface functional groups of the carbon black particles. If a carbon black with a DBP absorption number equal to or greater than 100 $cm^3$/100 g is used, the volatile content is low and the sensor sensitivity Rs/R0 will not exceed around 1.01. On the other hand, if a carbon black with a DBP absorption number less than 100 $cm^3$/100 g is used, the sensor sensitivity Rs/R0 increases as the volatile content increases. This is probably because the gap between the carbon black particles slightly changes depending on the number of the surface functional groups, thus causing a significant change in the amount of current flowing (electrical resistance caused) due to the tunneling effect. That is why the gas sensor 1 according to this embodiment preferably uses a carbon black with an undeveloped structure (i.e., having a low DBP absorption number) and a relatively large number of surface functional groups (volatile content) as its material. Specifically, the carbon black has a volatile content equal to or greater than 2.5 wt %, thus providing a sensitive membrane 20 and gas sensor 1 having high sensitivity. The upper limit of the volatile content of the carbon black is not set at any particular value but is preferably equal to or less than 8 wt %. As used herein, the volatile content refers to the volatile loss of the carbon black as a material when the carbon black is heated at 950° C. for 7 minutes.

Note that the volatile content may be measured by the method described in "Testing Methods of Carbon Black for Rubber Industry" according to the JIS K 6221 standard. Specifically, a specified amount of a carbon black is introduced into a crucible and heated at 950° C. for 7 minutes, and then the volatile loss of the carbon black is measured.

Alternatively, the volatile content may also be measured by performing mass spectrometry on the gas generated at an elevated temperature. Specifically, 1 mg of a sample is heated at a temperature increase rate of 10° C./min from room temperature to 1000° C. in a helium atmosphere and the gas generated is loaded into, and analyzed by, a mass spectrometer. Based on a gas emission profile (where m/z falls within the range from 10 to 600) thus obtained, m/z profiles (where m/z=18, 28, 44) of $H_2O$, CO, $N_2$, and $CO_2$, which are gases derived from the surface functional groups, are extracted. Then, each of these gases has its peak area compared with that of a reference material (such as sodium tungstate dihydrate or calcium oxalate monohydrate). In this manner, the volatile content may be quantified. Performing such a mass spectrometry on the gas generated at an elevated temperature allows the volatile content of even a small amount of sample to be calculated, thus enabling obtaining results comparable to the volatile content measuring method according to the JIS K 6221 standard.

Figure 7:
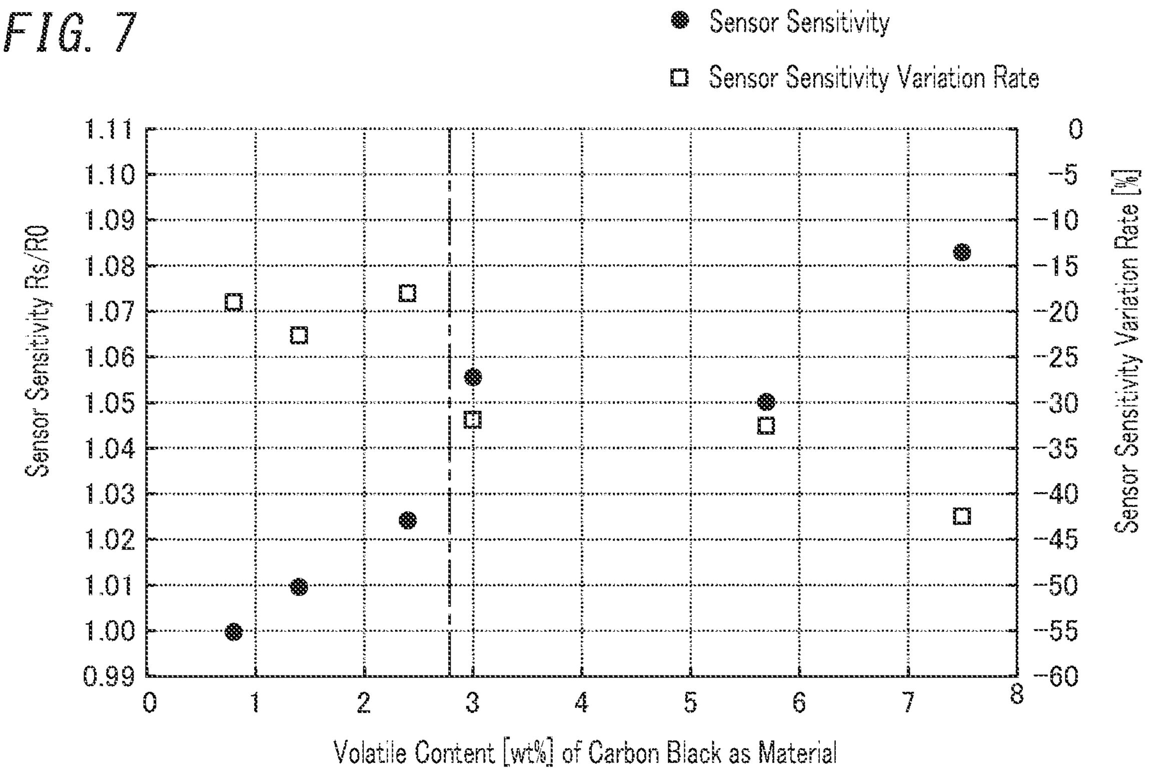
FIG. 7 is a graph showing how the sensor sensitivity and the sensor sensitivity variation rate change with the volatile content of the carbon black as the material for the gas sensor.

FIG. 7 shows how the sensor sensitivity Rs/R0 and the sensor sensitivity variation rate change with the volatile content of the carbon black as a material. The sensor sensitivity variation rate was obtained as follows. Specifically, after the initial characteristics (namely, the sensor resistance value and the sensor sensitivity) of the gas sensor 1 had been evaluated, the gas sensor 1 was stored in the air (at 25° C. and a RH of 40%) for two months. Then, the characteristics of the gas sensor 1 were evaluated as for the same parameters as the initial characteristics to calculate the variation rate from the initial characteristics after the gas sensor 1 had been stored for two months. In this embodiment, the volatile content of the carbon black is equal to or greater than 2.5 wt %. In that case, the sensor sensitivity is high enough to achieve an expected result, but the sensor sensitivity variation rate is relatively large. Thus, this material is suitably usable, for example, for a disposable gas sensor 1 (such as a gas sensor for use in a breath test), which is required to exhibit good sensor sensitivity but is not supposed to be stored for a long term.

In addition, according to this embodiment, even if the sensitive membrane 20 has adsorbed a very small amount of odor molecules, the gap between the carbon black particles (conductive particles 202) may also be widened sufficiently to cause a significant current variation. This makes it easier to detect the change in the resistance value of the sensitive membrane 20. Consequently, a gas sensor 1 including this sensitive membrane 20 may have its sensitivity increased.

Recapitulation

As can be seen from the foregoing description, a sensitive membrane (20) according to a first aspect includes: a membrane body (201) containing a sensitive material; and a carbon black contained in the membrane body (201). The carbon black has a volatile content equal to or greater than 2.5 wt %.

This aspect allows even a very small amount of odor molecules to be detected by the sensitive membrane (20), thus achieving the advantage of providing a high-sensitivity gas sensor.

In a sensitive membrane (20) according to a second aspect, which may be implemented in conjunction with the first aspect, the carbon black has a dibutyl phthalate absorption number less than 100 $cm^3/100$ g.

This aspect achieves the advantage of increasing the sensitivity of the gas sensor (1) because the carbon black has such an undeveloped structure that the sensitive membrane (20) causes electrical conduction by tunneling effect.

In a sensitive membrane (20) according to a third aspect, which may be implemented in conjunction with the first or second aspect, the carbon black has a Dst/D0 ratio less than 4, where Dst is a Stokes mode diameter of an aggregate as measured by centrifugal sedimentation analysis and D0 is a mean primary particle size.

This aspect achieves the advantage of increasing the sensitivity of the gas sensor (1) because the carbon black has such an undeveloped structure that the sensitive membrane (20) causes electrical conduction by tunneling effect.

In a sensitive membrane (20) according to a fourth aspect, which may be implemented in conjunction with any one of the first to third aspects, the membrane body (201) is expandable when adsorbing an analyte.

This aspect allows even a very small amount of odor molecules to be detected by the sensitive membrane (20), thus achieving the advantage of providing a high-sensitivity gas sensor.

A gas sensor (1) according to a fifth aspect includes: the sensitive membrane (20) according to any one of the first to fourth aspects; and an electrode (21) electrically connected to the sensitive membrane (20).

This aspect achieves the advantage of increasing the sensitivity of a gas sensor by using the sensitive membrane (20).

REFERENCE SIGNS LIST

1 Gas Sensor
20 Sensitive Membrane
201 Membrane Body
21 Electrode

The invention claimed is:

1. A sensitive membrane comprising:
a membrane body containing a sensitive material; and
a carbon black contained in the membrane body, wherein
the carbon black has a volatile content equal to or greater than 2.5 wt %,
the carbon black has a dibutyl phthalate absorption number less than 100 $cm^3/100$ g,
the carbon black is dispersed in the membrane body such that a change in a distance between particles of the carbon black caused by adsorption of an analyte changes an electrical resistance of the sensitive membrane.

2. The sensitive membrane of claim 1, wherein
the carbon black has a Dst/D0 ratio less than 4, where Dst is a Stokes mode diameter of an aggregate as measured by centrifugal sedimentation analysis and D0 is a mean primary particle size.

3. The sensitive membrane of claim 2, wherein
the membrane body is expandable when adsorbing the analyte.

4. A gas sensor comprising:
the sensitive membrane of claim 2; and
an electrode electrically connected to the sensitive membrane.

5. The sensitive membrane of claim 1, wherein
the membrane body is expandable when adsorbing the analyte.

6. A gas sensor comprising:
the sensitive membrane of claim 5; and
an electrode electrically connected to the sensitive membrane.

7. A gas sensor comprising:
the sensitive membrane of claim 1; and
an electrode electrically connected to the sensitive membrane.

8. The sensitive membrane of claim 1, wherein
the carbon black includes a surface functional group, and the surface functional group includes at least one selected from the group consisting of a carboxyl group, a hydroxyl group, and a quinone group.

9. The sensitive membrane of claim 1, wherein
the sensitive material includes at least one material selected from the group consisting of polyalkylene glycols, polyesters, glycerols, nitriles, dicarboxylic acid monoesters, and aliphatic amines.

10. The sensitive membrane of claim 1, wherein
the sensitive material includes at least one material selected from the group consisting of polyalkylene glycols, polyesters, glycerols, dicarboxylic acid monoesters, and aliphatic amines.

* * * * *